US00PP37184P2

(12) United States Plant Patent
Clarkson

(10) Patent No.: US PP37,184 P2
(45) Date of Patent: Dec. 30, 2025

(54) ***FRAGARIA* PLANT NAMED 'Eves Gloria'**

(50) Latin Name: ***Fragaria* x *ananassa***
Varietal Denomination: Eves Gloria

(71) Applicant: Graham Clarkson, Faversham (GB)

(72) Inventor: Graham Clarkson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 19/067,870

(22) Filed: Mar. 1, 2025

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

*Primary Examiner* — Susan McCormick Ewoldt
(74) *Attorney, Agent, or Firm* — Penny J. Aguirre

(57) ABSTRACT

A new cultivar of *Fragaria* plant named 'Eves Gloria' that is characterized by its high fruit yields with a very high percentage of that fruit being marketable as Class I, its vigorous growth habit with a dense canopy, its foliage that is strongly blistering, moderately glossy and relatively dark in color, its leaves that are predominantly concave in cross section, its fruit that is primarily conical in shape, highly glossy and large in size, and its fruit with moderate to high sugar levels and high juiciness.

3 Drawing Sheets

Botanical classification: *Fragaria* x *ananassa.*
Variety denomination: 'Eves Gloria'.

CROSS-REFERENCE TO A RELATED APPLICATION

This application is related to a European plant breeders' rights application filed on Jun. 1, 2023, application No. 2023/1190. The information for the Plant Breeders' Rights Application was received directly from the Inventor.

BACKGROUND OF THE INVENTION

The present invention relates to a new and distinct cultivar of *Fragaria*, botanically known as *Fragaria* x *ananassa* 'Eves Gloria' and will be referred to hereafter by its cultivar name, 'Eves Gloria'. 'Eves Gloria' is a day neutral strawberry plant primarily adapted to the climate and growing conditions of the United Kingdom and other regions of similar climate and day length for use in the fresh fruit market.

The new cultivar was derived from an ongoing breeding program conducted by the Inventor at a farm in Cartaya, Huelva, Spain. The goal of the breeding program was to develop a new cultivar of *Fragaria* having fruit with high yields, a large and uniform shape, firm skin, good eating quality with low acid content, and plants with consistent cropping combined with high disease tolerance. 'Eves Gloria' arose from a controlled cross made by the Inventor in spring of 2017 between an unpatented selection from the Inventors breeding program, designated as accession number "SZC33", as the female parent and an unpatented selection from the Inventor's breeding program, designated as accession number "SXP03", as the male parent. 'Eves Gloria' was selected as a single unique plant in Cartaya, Huelva, Spain in winter of 2018 from amongst the seedlings that resulted from the above cross.

Asexual propagation of the new cultivar was first accomplished by rooting stolons in Faversham, Kent, United Kingdom in summer of 2018. Asexual propagation by rooting of stolons and tissue culture using meristematic tissue has shown that the unique characteristics of the new cultivar are stable and reproduced true to type in successive generations.

SUMMARY OF THE INVENTION

The following traits have been repeatedly observed and represent the characteristics of the new cultivar. These attributes in combination distinguish 'Eves Gloria' as a unique cultivar of *Fragaria.*

1. 'Eves Gloria' exhibits high fruit yields with a very high percentage of that fruit being marketable as Class I.
2. 'Eves Gloria' exhibits a vigorous growth habit with a dense canopy.
3. 'Eves Gloria' exhibits foliage that is strongly blistering, moderately glossy and relatively dark in color.
4. 'Eves Gloria' exhibits leaves that are predominantly concave in cross section.
5. 'Eves Gloria' exhibits fruit that is primarily conical in shape, highly glossy and large in size.
6. 'Eves Gloria' exhibits fruit with moderate to high sugar levels and high juiciness.

The female parent of 'Eves Gloria' differs from 'Eves Gloria' in having a Lower Class I yield, fruit that is dryer (not as juicy), firmer with a crunchier texture, and paler in color. The male parent of 'Eves Gloria' differs from 'Eves Gloria' in having fruit with a lower sugar content and a less glossy surface, in producing a lower portion of its yield later in the season, and in having a less vigorous growth habit.

'Eves Gloria' can be compared to the *Fragaria* cultivars 'SRV36' (U.S. Plant Pat. No. 30,354) and 'Florida Radiance' (U.S. Plant Pat. No. 20,363). 'Eves Gloria' produces on average significantly higher Class I fruit yields than 'SRV36' throughout the season. The average fruit weight throughout the season is also significantly higher for 'Eves Gloria' compared to 'SRV36' and the variety 'Eves Gloria' also produces a larger amount of fruit earlier in the season than 'SRV36'. While both plants are semi-upright in their habit, the canopy of 'Eves Gloria' is generally significantly larger and denser than 'SRV36'. The crown size and number of crowns is greater on 'Eves Gloria' with 'Eves Gloria' generally producing a greater number of stolons. Both varieties produce fruit that is conical in shape and larger length in relation to width. The calyx size in relation to fruit size is similar in both 'Eves Gloria' and 'SRV36'; at the start of cropping, the calyx is significantly larger than the fruit diameter and later in the season, the calyx size is similar to the fruit diameter. However, because the fruit of 'Eve Gloria' is generally larger than 'SRV36', the average calyx size is also generally larger. The calyx of both varieties strongly adheres to the fruit, however the calyx of 'SRV36' is mostly recurved in relation to fruit whereas the calyx of 'Eves Gloria' is mostly level. The fruit of 'Eves Gloria' is a darker shade of red and is glossier when compared to the fruit of 'SRV36'. Both varieties lack a band without achenes on the shoulder of the fruit 'Eves Gloria' has slightly more achenes per fruit than 'SRV36'. Both 'Eves Gloria' and 'SRV36' have fruits that is highly sweet, however the brix levels on 'SRV36' are on average higher across the season than those recorded in 'Eves Gloria'.

While both varieties exhibit good shelf life, the fruit skin firmness of 'SRV36' is generally higher than that of 'Eves Gloria'. The fruit of 'Eves Gloria' is generally juicier than 'SRV36' and has a softer fruit texture. The leaves of both varieties also exhibit different characteristics. Due to the denser nature of 'Eves Gloria', there are generally more leaves per plant on 'Eves Gloria' than 'SRV36'. While the leaves of 'Eves Gloria' and 'SRV36' are generally similar in average width, the average length of 'Eves Gloria' leaves is longer, resulting in a more elongated leaf shape in 'Eves Gloria'. The leaves of 'Eves Gloria' also exhibit more blistering and have on average fewer serrations per leaflet than 'SRV36'. While the glossiness of the leaf surface for both varieties is similar, the upper leaf color of 'Eves Gloria' is a darker shade of green. Additional differences can be observed in the petiole, whereby the length and thickness is greater in 'Eves Gloria' than in 'SRV36' and 'Eves Gloria' exhibits moderate surface pubescence and 'SRV36' exhibits moderate to heavy surface pubescence. The petiolule is longer in 'Eves Gloria', but thicker in 'SRV36'. In both varieties, flowering is temperature and day-length dependent, however in 'Eves Gloria' flowering is generally observed earlier in the season the 'SRV36'. Both varieties tend to express their flowers above the leaf canopy, with the overall length of the truss greater in 'Eves Gloria' than in 'SRV36'. Pedicel pubescence is similar between the two varieties but peduncle pubescence is heavier in 'Eves Gloria' than in 'SRV36'. On average, the number of trusses and the number of fruit per truss is greater in 'Eves Gloria'. The petals of 'Eves Gloria' are smaller on average than those of 'SRV36'. 'Eves Gloria' generally has more sepals per flower and also expresses sepals that are a slightly paler shade of green than 'SRV36'. 'Florida Radiance' is similar to 'Eves Gloria' in having fruit that is highly juicy and primarily conical in shape. 'Florida Radiance' differs from 'Eves Gloria' in having fruit with less skin firmness, skin with a deeper shape of red, an earlier fruiting season, and a less vigorous growth habit.

BRIEF DESCRIPTION OF THE DRAWINGS

The accompanying color photographs illustrate the overall appearance and distinct characteristics of the new *Fragaria*. The photographs were taken of 5-month-old plants of 'Eves Gloria' as grown outdoors in raised beds under tunnels with polyethylene covers in Cartaya, Huelva, Spain.

The photograph in FIG. 1 provides a view of 'Eves Gloria' bearing fruit.

Figure 1:
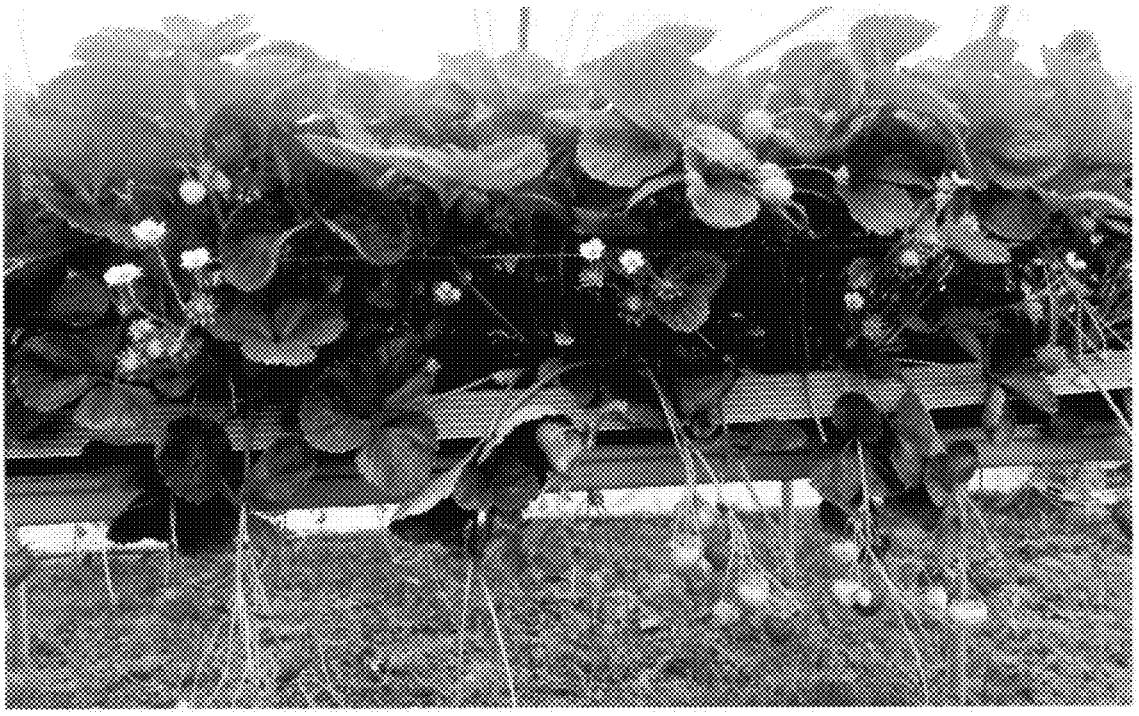
Figure 2:
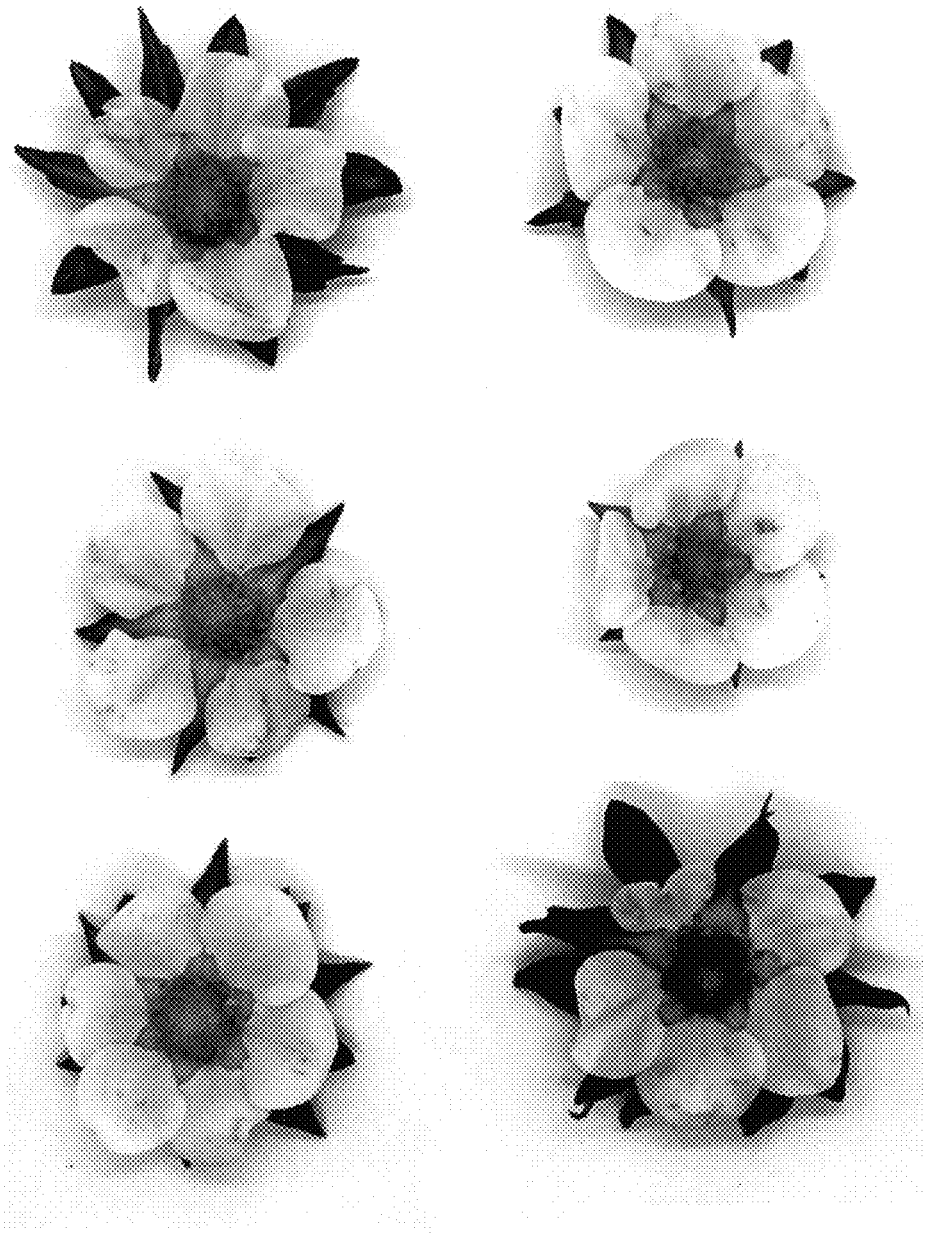

The photograph in FIG. 2 provides a close-up view of the flowers of 'Eves Gloria'.

Figure 3:
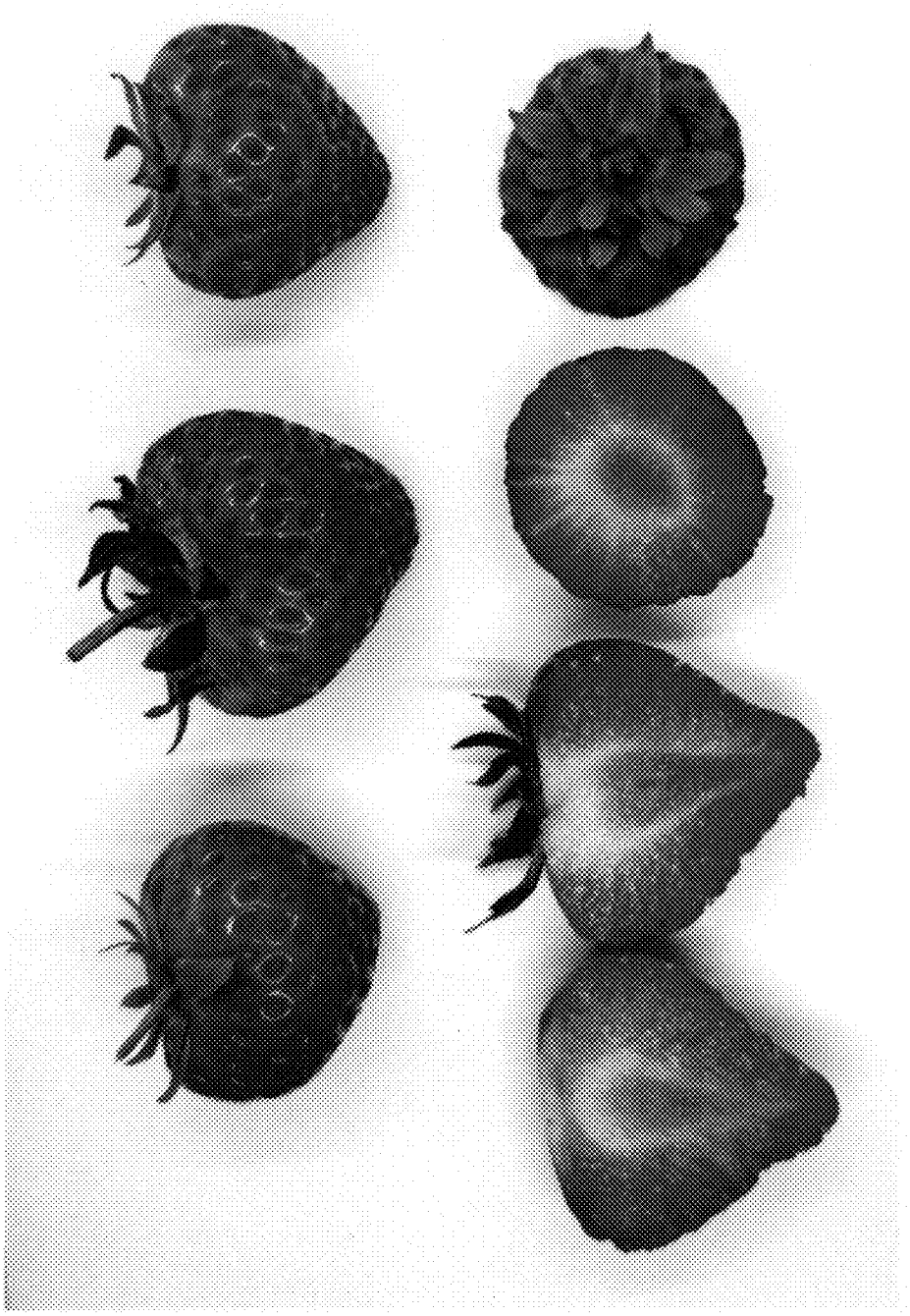

The photograph in FIG. 3 provides a close-up view of the whole fruit of 'Eves Gloria' (right) and longitudinal and horizontal cross sections (left) of the fruit.

The colors in the photographs are as close as possible with the photographic and printing technology utilized and the color values cited in the detailed botanical description accurately describe the colors of the new *Fragaria*.

BOTANICAL DESCRIPTION OF THE PLANT

The following is a detailed description of 5-month-old plants of 'Eves Gloria' as grown outdoors in the soil, in raised beds, under tunnels with polyethylene covers in Cartaya, Huelva, Spain. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Early January through mid-May in Cartaya, Huelva, Spain.

*Plant type.*—Herbaceous fruit producing perennial.

*Plant habit.*—Semi-upright, with a dense canopy.

*Height and spread.*—Medium to large in size; reaches average of 28.8 cm in height and 44.7 cm in width, with an average height to width ratio of about 0.6:1 as a 5-month-old plant.

*Crown.*—Average total diameter of 5.2 cm with an average crown number of 5.

*Cold hardiness.*—Not tested in areas where temperatures of less than 32° occur.

*Diseases and pests.*—Tolerance to *Botryotinia cinerea* and moderate susceptibility to *Podosphaera leucotricha* (powdery mildew) has been observed, no susceptibility or resistance to pests has been observed.

*Root description.*—Fibrous, N155D in color.

*Root development.*—An average of 2 weeks to initiate roots and 5 weeks to produce a young, rooted plant.

*Propagation.*—Rooting of stolons and tissue culture.

*Growth rate.*—Vigorous.

*Stem description.*—Acaulescent.

*Stolon description.*—Produces stolons throughout the cropping season; surface pubescence is sparse to medium.

*Stolon color.*—146B, medium anthocyanin 176A.

Foliage description:

*Leaf division*.—Three leaflets.

*Leaf arrangement*.—Basal.

*Leaf attachment*.—Petiolate.

*Leaflet shape*.—Rounded.

*Mid-tier terminal leaflet size*.—Average of 7.4 cm in length and 6.9 cm in width, average length to width ratio of 1.1:1

*Leaflet margins*.—Serrate to crenate with an average of 25.5 serrations per leaf.

*Leaflet base*.—Acute.

*Leaflet apex*.—Round.

*Leaflet glossiness*.—Medium.

*Leaflet aspect*.—Concave.

*Leaflet interveinal blistering*.—Strong.

*Leaflet venation*.—Pinnate, coloration matches leaflet color.

*Leaflet surface*.—Upper surface glabrous, lower surface very slightly pubescent, particularly along the vein.

*Leaflet color*.—Upper surface 137A, lower surface 138B, no variegation present on either surface.

*Petiole*.—Round in shape, average of 21.2 cm in length and 5.4 mm in width, 144C in color, moderately pubescent surface with most hairs horizontal in attitude.

*Petiolules*.—Round in shape, average of 7 mm in length and 2 mm in width, strong pubescence on surfaces, 144D in color.

*Stipule*.—Average of 3.6 cm in length and 1.8 cm in width, weak anthocyanin 49B in color.

*Variegation*.—Absent.

Flower description:

*Inflorescence*.—Truss.

*Pedicel*.—Average of 5.1 cm in length and 2 mm in width, 144C in color, has a weak to moderate level of pubescence, held in a slightly upwards hair attitude.

*Peduncle*.—Average of 15.1 cm in length and 3.4 mm in width, 144C in color, moderately pubescent surface with a horizontal hair attitude, strong in strength.

*Flower initiation and expression conditions*.—Temperature dependent and day length dependent.

*Time of flowering* (50% *of plants at first flower*).—Early-mid season.

*Flower position relative to foliage*.—Mostly above the level of the leaf canopy.

*Flower size*.—Average of 2.8 cm in diameter.

*Flower number per truss*.—Average 4.6.

*Flower fragrance*.—Weak.

*Calyx*.—Average of 3.5 cm in diameter, generally larger than the corolla.

*Sepals*.—Average of 12.1 per flower, with an obtuse base and an acute apex, the adaxial color is 137A, while the abaxial color 138A, average length of 1.3 cm, average width of 6 mm, adaxial pubescence weak, abaxial pubescence strong, held in a mixed arrangement relative to the fruit, mostly horizontal with fruit shoulder to slightly inverted.

*Petals*.—Average of 6, average of 1.2 cm in length and 1.3 cm in width, rounded in shape, acute base, obtuse apex, overlapping in their arrangement, entire margins, upper and lower surface glabrous and NN155D in color.

Reproductive organs:

*Gynoecium*.—Average of 7.4 mm in height and 6.4 mm in width, with a steeply dome shaped and slightly pointed top, multiple simple pistils present with capitate shaped stigma, stigma color 150C.

*Androecium*.—Stamens; average of 29.7 per flower, anthers; average of 1.4 mm in length and 9.4 mm in diameter, 13A in color, filament; 1.9 mm in length and 0.7 mm in diameter, 154C in color, pollen; moderate in quantity, 2A in color.

Fruit description:

*Shape*.—Predominantly conical, shape is similar for primary, secondary and tertiary fruit.

*Season of harvest*.—January through mid-May in Cartaya, Huelva, Spain.

*Time of ripening* (50% *of plants with first ripe fruit*).—Early-mid season.

*Type of bearing*.—Short day in mediterranean climates (dry summers and wet but mild winters).

*Size*.—An average of 5.2 cm in length and 4.2 cm in width.

*Surface*.—Smooth with strong and even glossiness.

*Calyx position*.—Generally level with fruit.

*Attitude of calyx segments*.—Mostly outwards with strong adherence to the fruit.

*Diameter of calyx relative to fruit diameter*.—Calyx is slightly larger than the fruit diameter.

*External color* (*skin*).—34B, color is retained throughout the cropping season.

*Internal color* (*flesh*).—Near skin; 44B, near center; 31A.

*Evenness of color of skin*.—Very even.

*Evenness of color of flesh*.—Paler near center.

*Acidity*.—Medium.

*Sweetness*.—Moderate to high.

*Soluble solids*.—Average of 9.1° over three seasons in trials.

*Firmness*.—Skin is firm (resistant to bruising), flesh is firm.

*Juiciness*.—High.

*Aroma*.—None.

*Weight*.—Average of 21.2 g per berry and 1256g per plant to end of April over three seasons in trials.

*Number of fruits per plant*.—Average 59 fruits per plant to end of April over three seasons in trials.

*Hollow center*.—Slight on primary, secondary and tertiary fruit, more prominent on primary fruit, average of 1.3 cm in length and 4 mm in width.

*Shelf life*.—Very good, an average of 7 days in cold storage.

*Achene color*.—Predominantly 151B.

*Achene position*.—Majority below surface of fruit.

*Achene number*.—An average of 254 per berry.

*Band without achenes*.—Absent.

*Fruit use*.—Fresh fruit market.

It is claimed:

1. A new and distinct cultivar of *Fragaria* plant named 'Eves Gloria' substantially as herein illustrated and described.

* * * * *